United States Patent
Jain et al.

(10) Patent No.: US 10,420,514 B2
(45) Date of Patent: Sep. 24, 2019

(54) DETECTION OF CHRONOTROPIC INCOMPETENCE

(71) Applicant: Samsung Electronics Co., Ltd., Gyeonggi-Do (KR)

(72) Inventors: Jawahar Jain, Los Altos, CA (US); Cody Wortham, Mountain View, CA (US); James Young, Menlo Park, CA (US); Sajid Sadi, San Jose, CA (US); Pranav Mistry, Campbell, CA (US)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 165 days.

(21) Appl. No.: 15/296,689

(22) Filed: Oct. 18, 2016

(65) Prior Publication Data

US 2017/0245805 A1    Aug. 31, 2017

Related U.S. Application Data

(60) Provisional application No. 62/300,024, filed on Feb. 25, 2016.

(51) Int. Cl.
*A61B 5/00* (2006.01)
*A61B 5/024* (2006.01)
(Continued)

(52) U.S. Cl.
CPC ............ *A61B 5/7275* (2013.01); *A61B 5/024* (2013.01); *A61B 5/02055* (2013.01);
(Continued)

(58) Field of Classification Search
CPC ... A61B 5/7275; A61B 5/02055; A61B 5/024; A61B 5/1118; A61B 5/003; A61B 5/08; A61B 5/681
See application file for complete search history.

(56) References Cited

U.S. PATENT DOCUMENTS

| | | |
|---|---|---|
| 5,144,949 A | 9/1992 | Olson |
| 5,410,472 A | 4/1995 | Anderson |

(Continued)

FOREIGN PATENT DOCUMENTS

| | | |
|---|---|---|
| CN | 104840191 A | 8/2015 |
| EP | 0559847 A1 | 9/1993 |

(Continued)

OTHER PUBLICATIONS

U.S. Appl. No. 15/436,920, Non-Final Office Action, dated Mar. 7, 2018, 11 pg.

(Continued)

*Primary Examiner* — Paula J Stice
(74) *Attorney, Agent, or Firm* — Cuenot, Forsythe & Kim, LLC

(57) ABSTRACT

Detecting chronotropic incompetence includes determining, using a processor, a baseline cardiac health measure for a user based upon an estimate of activity level for the user, validating, using the processor, the estimate of activity level for the user with a validation factor determined from sensor data and determining, using the processor, a cardiac health measure for the user from the sensor data. A signal indicating chronotropic incompetence for the user can be provided by the processor based upon a comparison of the cardiac health measure for the user with the baseline cardiac health measure.

27 Claims, 3 Drawing Sheets

(51) Int. Cl.
  *A61B 5/11*       (2006.01)
  *A61B 7/00*       (2006.01)
  *A61B 5/0205*     (2006.01)
  *A61B 5/08*       (2006.01)
  *G16H 50/30*      (2018.01)

(52) U.S. Cl.
  CPC ............ *A61B 5/1118* (2013.01); *A61B 7/003* (2013.01); *A61B 5/08* (2013.01); *G16H 50/30* (2018.01)

(56) References Cited

U.S. PATENT DOCUMENTS

| | | | |
|---|---|---|---|
| 6,077,222 | A  | 6/2000  | Lloyd et al. |
| 6,190,324 | B1 | 2/2001  | Kieval et al. |
| 6,472,988 | B1 | 10/2002 | Feld et al. |
| 6,540,674 | B2 | 4/2003  | Zadrozny et al. |
| 6,904,311 | B2 | 6/2005  | Freeberg |
| 7,142,920 | B2 | 11/2006 | Scheiner et al. |
| 7,674,226 | B2 | 3/2010  | Nadeau |
| 7,785,242 | B2 | 8/2010  | Solomon |
| 7,853,455 | B2 | 12/2010 | Brown |
| 7,869,877 | B2 | 1/2011  | Kadhiresan et al. |
| 7,877,277 | B1 | 1/2011  | Petit et al. |
| 7,974,708 | B2 | 7/2011  | Daum et al. |
| 7,993,268 | B2 | 8/2011  | Nadeau |
| 8,118,712 | B2 | 2/2012  | Thieberger et al. |
| 8,200,323 | B2 | 6/2012  | Dibenedetto et al. |
| 8,660,625 | B2 | 2/2014  | Addison et al. |
| 8,719,214 | B2 | 5/2014  | Stergiou et al. |
| 8,738,133 | B2 | 5/2014  | Shuros et al. |
| 8,768,489 | B2 | 7/2014  | Thieberger et al. |
| 8,781,564 | B2 | 7/2014  | Kinnunen |
| 8,876,688 | B2 | 11/2014 | Hyde et al. |
| 8,897,522 | B2 | 11/2014 | Mestha et al. |
| 8,903,491 | B2 | 12/2014 | Hopper et al. |
| 8,956,290 | B2 | 2/2015  | Gilley et al. |
| 8,972,013 | B2 | 3/2015  | Maschino |
| 8,986,206 | B2 | 3/2015  | Kim et al. |
| 9,002,427 | B2 | 4/2015  | Tupin, Jr. et al. |
| 9,020,185 | B2 | 4/2015  | Mestha et al. |
| 9,027,552 | B2 | 5/2015  | Angelico et al. |
| 9,028,258 | B2 | 5/2015  | Burdea |
| 9,035,778 | B2 | 5/2015  | Howie et al. |
| 9,070,267 | B2 | 6/2015  | Hanson et al. |
| 9,089,760 | B2 | 7/2015  | Tropper et al. |
| 9,106,307 | B2 | 8/2015  | Molettiere et al. |
| 9,128,305 | B2 | 9/2015  | Honore et al. |
| 9,132,275 | B2 | 9/2015  | Yu et al. |
| 9,135,347 | B2 | 9/2015  | Dammen et al. |
| 9,161,698 | B2 | 10/2015 | Zhang et al. |
| 9,168,017 | B2 | 10/2015 | Ward et al. |
| 9,171,196 | B2 | 10/2015 | Wang et al. |
| 9,173,615 | B2 | 11/2015 | Katra et al. |
| 9,180,140 | B2 | 11/2015 | Lundberg et al. |
| 9,185,353 | B2 | 11/2015 | Mestha et al. |
| 9,204,836 | B2 | 12/2015 | Bender |
| 9,220,440 | B2 | 12/2015 | Addison et al. |
| 9,232,894 | B2 | 1/2016  | Tesanovic et al. |
| 9,232,897 | B2 | 1/2016  | Thakur et al. |
| 9,232,910 | B2 | 1/2016  | Alshaer et al. |
| 9,247,884 | B2 | 2/2016  | Yuen et al. |
| 9,248,306 | B2 | 2/2016  | Joo et al. |
| 9,250,104 | B2 | 2/2016  | Greiner et al. |
| 9,262,772 | B2 | 2/2016  | Stivoric et al. |
| 9,265,477 | B2 | 2/2016  | Yang et al. |
| 9,268,908 | B2 | 2/2016  | Ashdown et al. |
| 9,286,789 | B2 | 3/2016  | Park et al. |
| 9,294,898 | B2 | 3/2016  | Shikama et al. |
| 9,665,873 | B2 | 5/2017  | Ackland et al. |
| 10,172,517 | B2 | 1/2019 | Jain et al. |
| 2004/0006492 | A1 | 1/2004 | Watanage |
| 2005/0070809 | A1 | 3/2005 | Acres |
| 2005/0267541 | A1 | 12/2005 | Scheiner et al. |
| 2006/0218007 | A1 | 9/2006 | Bjorner et al. |
| 2007/0024946 | A1 | 2/2007 | Panasyuk et al. |
| 2007/0179350 | A1 | 8/2007 | Nadeau |
| 2007/0185391 | A1 | 8/2007 | Morgan |
| 2007/0207437 | A1 | 9/2007 | Sachdeva et al. |
| 2008/0150714 | A1 | 6/2008 | Bauer et al. |
| 2009/0058660 | A1 | 3/2009 | Torch |
| 2009/0076343 | A1 | 3/2009 | James et al. |
| 2009/0234406 | A1 | 9/2009 | Shuros et al. |
| 2009/0271347 | A1 | 10/2009 | Hyde et al. |
| 2009/0312151 | A1 | 12/2009 | Thieberger et al. |
| 2009/0312658 | A1 | 12/2009 | Thieberger |
| 2010/0009328 | A1 | 1/2010 | Nadeau |
| 2010/0249531 | A1 | 9/2010 | Hanlon et al. |
| 2010/0256512 | A1 | 10/2010 | Sullivan |
| 2010/0292599 | A1 | 11/2010 | Oleson et al. |
| 2010/0292600 | A1 | 11/2010 | Dibenedetto et al. |
| 2010/0298899 | A1 | 11/2010 | Donnelly et al. |
| 2011/0270049 | A1* | 11/2011 | Katra .................. A61B 5/0002 600/301 |
| 2011/0275942 | A1 | 11/2011 | Stahmann et al. |
| 2011/0295084 | A1 | 12/2011 | Thakur et al. |
| 2012/0010504 | A1 | 1/2012 | Furlan |
| 2012/0029936 | A1 | 2/2012 | Hanoun |
| 2012/0109243 | A1 | 5/2012 | Hettrick et al. |
| 2012/0145152 | A1 | 6/2012 | Lain et al. |
| 2012/0157856 | A1 | 6/2012 | An et al. |
| 2012/0253207 | A1 | 10/2012 | Sarkar et al. |
| 2012/0259649 | A1 | 10/2012 | Mallon et al. |
| 2013/0024212 | A1 | 1/2013 | Atakhorrami et al. |
| 2013/0079646 | A1 | 3/2013 | Bhunia et al. |
| 2013/0092165 | A1 | 4/2013 | Wondka |
| 2013/0197381 | A1 | 8/2013 | Charlton et al. |
| 2013/0209977 | A1 | 8/2013 | Lathan et al. |
| 2013/0261479 | A1 | 10/2013 | Kemppainen et al. |
| 2013/0281798 | A1 | 10/2013 | Rau et al. |
| 2014/0006041 | A1 | 1/2014 | Steinhauer et al. |
| 2014/0051047 | A1 | 2/2014 | Bender et al. |
| 2014/0051941 | A1 | 2/2014 | Messerschmidt |
| 2014/0052475 | A1 | 2/2014 | Madan et al. |
| 2014/0058745 | A1 | 2/2014 | Ji et al. |
| 2014/0061047 | A1 | 3/2014 | Stich et al. |
| 2014/0081432 | A1 | 3/2014 | Kingon et al. |
| 2014/0100822 | A1 | 4/2014 | Hiltner |
| 2014/0107500 | A1 | 4/2014 | Stamatopoulos et al. |
| 2014/0112559 | A1 | 4/2014 | Freeman et al. |
| 2014/0114147 | A1 | 4/2014 | Romesburg |
| 2014/0149465 | A1 | 5/2014 | Kannan et al. |
| 2014/0155773 | A1 | 6/2014 | Stamatopoulos et al. |
| 2014/0171776 | A1 | 6/2014 | Lin et al. |
| 2014/0172442 | A1 | 6/2014 | Broderick et al. |
| 2014/0228649 | A1 | 8/2014 | Rayner et al. |
| 2014/0243686 | A1 | 8/2014 | Kimmel |
| 2014/0267668 | A1 | 9/2014 | Ignatovich et al. |
| 2014/0276549 | A1 | 9/2014 | Osorio |
| 2014/0371604 | A1 | 12/2014 | Katra et al. |
| 2015/0011361 | A1 | 1/2015 | Boyette et al. |
| 2015/0031965 | A1 | 1/2015 | Visvanathan et al. |
| 2015/0038854 | A1 | 2/2015 | Zhang et al. |
| 2015/0065825 | A1 | 3/2015 | Utley et al. |
| 2015/0065898 | A1 | 3/2015 | Prstojevich et al. |
| 2015/0099952 | A1 | 4/2015 | Lain et al. |
| 2015/0125832 | A1 | 5/2015 | Tran |
| 2015/0141767 | A1 | 5/2015 | Rogers et al. |
| 2015/0165271 | A1 | 6/2015 | Sung-Lien et al. |
| 2015/0202492 | A1 | 7/2015 | Domansky et al. |
| 2015/0213217 | A1 | 7/2015 | Amarasingham et al. |
| 2015/0269851 | A1 | 9/2015 | Lee et al. |
| 2015/0286857 | A1 | 10/2015 | Kim et al. |
| 2015/0305675 | A1 | 10/2015 | Miller et al. |
| 2015/0305683 | A1 | 10/2015 | Friat Filing et al. |
| 2015/0317438 | A1 | 11/2015 | Ingrassia, Jr. et al. |
| 2015/0352147 | A1 | 12/2015 | Lundberg et al. |
| 2015/0359845 | A1 | 12/2015 | Marban et al. |
| 2015/0370993 | A1 | 12/2015 | Moturu et al. |
| 2015/0370994 | A1 | 12/2015 | Madan et al. |
| 2015/0374289 | A1 | 12/2015 | Teller et al. |
| 2015/0379477 | A1 | 12/2015 | Junqua et al. |
| 2016/0008957 | A1 | 1/2016 | Kaur et al. |
| 2016/0022193 | A1 | 1/2016 | Rau et al. |

(56) References Cited

U.S. PATENT DOCUMENTS

| | | | |
|---|---|---|---|
| 2016/0045168 A1 | 2/2016 | Storer et al. |
| 2016/0058336 A1 | 3/2016 | Blahnik et al. |
| 2016/0063205 A1 | 3/2016 | Moturu et al. |
| 2016/0091922 A1 | 3/2016 | Nazzaro et al. |
| 2016/0317044 A1 | 11/2016 | Wu |
| 2016/0345841 A1 | 12/2016 | Jang et al. |
| 2016/0354636 A1 | 12/2016 | Jang et al. |
| 2017/0245759 A1 | 8/2017 | Jain et al. |
| 2017/0245808 A1 | 8/2017 | Jain et al. |
| 2017/0249437 A1 | 8/2017 | Jain et al. |
| 2017/0249438 A1 | 8/2017 | Jain et al. |
| 2017/0282011 A1 | 10/2017 | Jang et al. |
| 2017/0296104 A1 | 10/2017 | Ryan et al. |

FOREIGN PATENT DOCUMENTS

| | | |
|---|---|---|
| EP | 1192971 A2 | 8/2001 |
| EP | 1667578 A1 | 9/2004 |
| EP | 2739207 A2 | 6/2014 |
| EP | 2897067 A1 | 7/2015 |
| KR | 20000006830 A | 2/2000 |
| KR | 100545772 B1 | 1/2006 |
| KR | 20060092557 A | 8/2006 |
| KR | 20130010207 A | 1/2013 |
| RU | 2462985 C1 | 10/2012 |
| WO | 9216258 A1 | 10/1992 |
| WO | 01008755 A1 | 2/2001 |
| WO | 02018019 A1 | 3/2002 |
| WO | 2011032132 A2 | 3/2011 |
| WO | 2013036853 A2 | 3/2013 |
| WO | 20140147496 A1 | 9/2014 |
| WO | 2015178637 A1 | 11/2015 |
| WO | 2016049425 A1 | 3/2016 |

OTHER PUBLICATIONS

Int'l. Appln. No. PCT/KR2017/002043, Int'l. Search Report, dated Apr. 28, 2017, 3 pg.

Int'l. Appln. No. PCT/KR2017/002043, Written Opinion, dated Apr. 28, 2017, 8 pg.

Int'l. Appln. No. PCT/KR2017/002067, Written Opinion, dated May 29, 2017, 7 Pg.

Int'l. Appln. No. PCT/KR2017/002039, Int'l. Search Report, dated May 23, 2017, 3 pg.

Int'l. Appln. No. PCT/KR2017/002039, Written Opinion, dated May 23, 2017, 5 pg.

Int'l. Appln. No. PCT/KR2017/002055, Int'l. Search Report and Written Opinion, dated May 29, 2017, 13 pg.

Int'l. Appln. No. PCT/KR2017/002067, Int'l Search Report, dated May 29, 2017, 7 Pg.

Web Cam Used to Detect Abnormal Heart Rhythm, [online] Reuters Health, in the Journal of mHealth, Oct. 15, 2014., vol. 1, No. 5, pp. 16-17, retrieved from the Internet: <https://www.joomag.com/magazine/the-journal-of-mhealth-vol-1-issue-5-oct-2014/0194692001413453930?page=18>.

Lauer, M.S., "Heart Rate Response in Stress Testing: Clinical Implications," In ACC Current Journal Review, vol. 10, No. 5, pp. 16-19, Oct. 31, 2001.

Int'l. Appln. No. PCT/KR2016/014583A1, Int'l. Search Report and Written Opinion, dated Mar. 14, 2017, 11 pg.

Lee, J. et al., "Atrial Fibrillation Detection using a Smart Phone," in 34th Annual Int'l. Conf. of the IEEE Engineering in Medicine and Biology Society (EMBC), Sep. 1, 2012, pp. 1177-1180.

Melzer, C. et al, Predictors of Chronotropic Incompetence in the Pacemaker Patient Population, in Europace, vol. 8, No. 1, Jan. 2006. pp. 70-75.

Melzer, C. et al., "Chronotropic Incompetence: a Never-Ending Story," in Europace, vol. 12, No. 4, Apr. 2010, pp. 464-465.

U.S. Appl. No. 15/436,054, Non-Final Office Action, dated Aug. 14, 2018, 14 pg.

U.S. Appl. No. 15/436,920, Notice of Allowance, dated Aug. 29, 2018, 8 pg.

U.S. Appl. No. 15/436,054, Notice of Allowance, dated Mar. 11, 2019, 11 pg.

EP Appln. EP17756857.3, Extended European Search Report, dated Jan. 2, 2019, 7 pg.

EP Appln. EP16891765.6, Extended European Search Report, dated Jan. 7, 2019, 9 pg.

Wilkoff, B.L. et al., "A Mathematical Model of the Cardiac Chronotropic Response to Exercise," Journal of Cardiovascular Electrophysiol, Futura Publishing Co., vol. 3, No. 3, Jun. 1, 1989, pp. 176-180.

Guerra, M. et al., "Chronotropic incompetence in persons with down syndrome," Archives of Physical Medicine and Rehabilitation, vol. 8, No. 11, Nov. 1, 2003, pp. 160-1608.

EP Appln. No. 17756862.3, Extended European Search Report, dated Feb. 5, 2019, 11 pg.

EP Appln. No. 17756850.8, Extended European Search Report, dated Feb. 6, 2019, 9 pg.

\* cited by examiner

DETECTION OF CHRONOTROPIC INCOMPETENCE

CROSS-REFERENCE TO RELATED APPLICATIONS

This application claims the benefit of U.S. Provisional Patent Application No. 62/300,024 filed on Feb. 25, 2016, which is fully incorporated herein by reference.

RESERVATION OF RIGHTS IN COPYRIGHTED MATERIAL

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

This disclosure relates to detecting cardiac disease within individuals and, more particularly, to detecting chronotropic incompetence.

BACKGROUND

Chronotropic incompetence (CI), broadly speaking, is the inability of the heart to increase its heart rate commensurate with increased activity or demand. CI is a problem that affects patients suffering from a variety of different cardiovascular diseases. For example, CI can affect approximately a third or more of heart-failure patients. CI can affect an even larger percentage of patients that have a pacemaker.

When an individual has a chronotropically competent heart rate response (e.g., the individual does not have CI), cardiac output is increased in response to exertion to meet the increased metabolic demands of the body. When an individual has CI, cardiac output is limited and unable to meet the increased metabolic demands of the body from exertion. CI can limit the amount of activity, whether exercise or daily tasks, a person can undertake without feeling tired. As such, CI can significantly limit the quality of one's life. CI is also correlated with cardiovascular mortality.

SUMMARY

One or more embodiments are directed to methods of detecting chronotropic incompetence (CI). In one aspect, a method can include determining a baseline cardiac health measure for a user based upon an estimate of activity level for the user, validating the estimate of activity level for the user with a validation factor determined from sensor data, and determining a cardiac health measure for the user from the sensor data. The method can include providing, using the processor, a signal indicating CI for the user based upon a comparison of the cardiac health measure for the user with the baseline cardiac health measure.

In another aspect, a method can include determining a baseline cardiac health measure for a user, determining a cardiac health measure for the user from the sensor data, and providing, using the processor, a signal indicating CI for the user based upon a comparison of the cardiac health measure for the user with the baseline cardiac health measure.

In one or more embodiments, the baseline cardiac health measure and the cardiac health measure each includes a covariance. The covariances may involve, for example, heart rate of the user, a measure of total activity for a user determined from the sensor data, a rating of perceived exertion for the user, heart rate recovery of the user, and so forth.

One or more embodiments are directed to apparatus for detecting CI. In one aspect, an apparatus includes a sensor configured to generate sensor data, a memory configured to store the sensor data, and a processor, coupled to the memory and the sensor, configured to determine a baseline cardiac health measure for a user based upon an estimate of activity level for the user, validate the estimate of activity level for the user with a validation factor determined from the sensor data, and determine a cardiac health measure for the user from the sensor data. The processor is further configured to provide a signal indicating CI for the user based upon a comparison of the cardiac health measure for the user with the baseline cardiac health measure.

One or more embodiments are directed to computer program products for detecting CI. In one aspect, a computer program product includes a computer readable storage medium having program code stored thereon. The program code is executable by a processor to perform executable operations. The executable operations can include determining a baseline cardiac health measure for a user based upon an estimate of activity level for the user, validating the estimate of activity level for the user with a validation factor determined from sensor data, and determining a cardiac health measure for the user from the sensor data. The executable operations can include providing a signal indicating CI for the user based upon a comparison of the cardiac health measure for the user with the baseline cardiac health measure.

This Summary section is provided merely to introduce certain concepts and not to identify any key or essential features of the claimed subject matter. Many other features and embodiments of the invention will be apparent from the accompanying drawings and from the following detailed description.

BRIEF DESCRIPTION OF THE DRAWINGS

The accompanying drawings show one or more embodiments; however, the accompanying drawings should not be taken to limit the invention to only the embodiments shown. Various aspects and advantages will become apparent upon review of the following detailed description and upon reference to the drawings.

DETAILED DESCRIPTION

Figure 1:
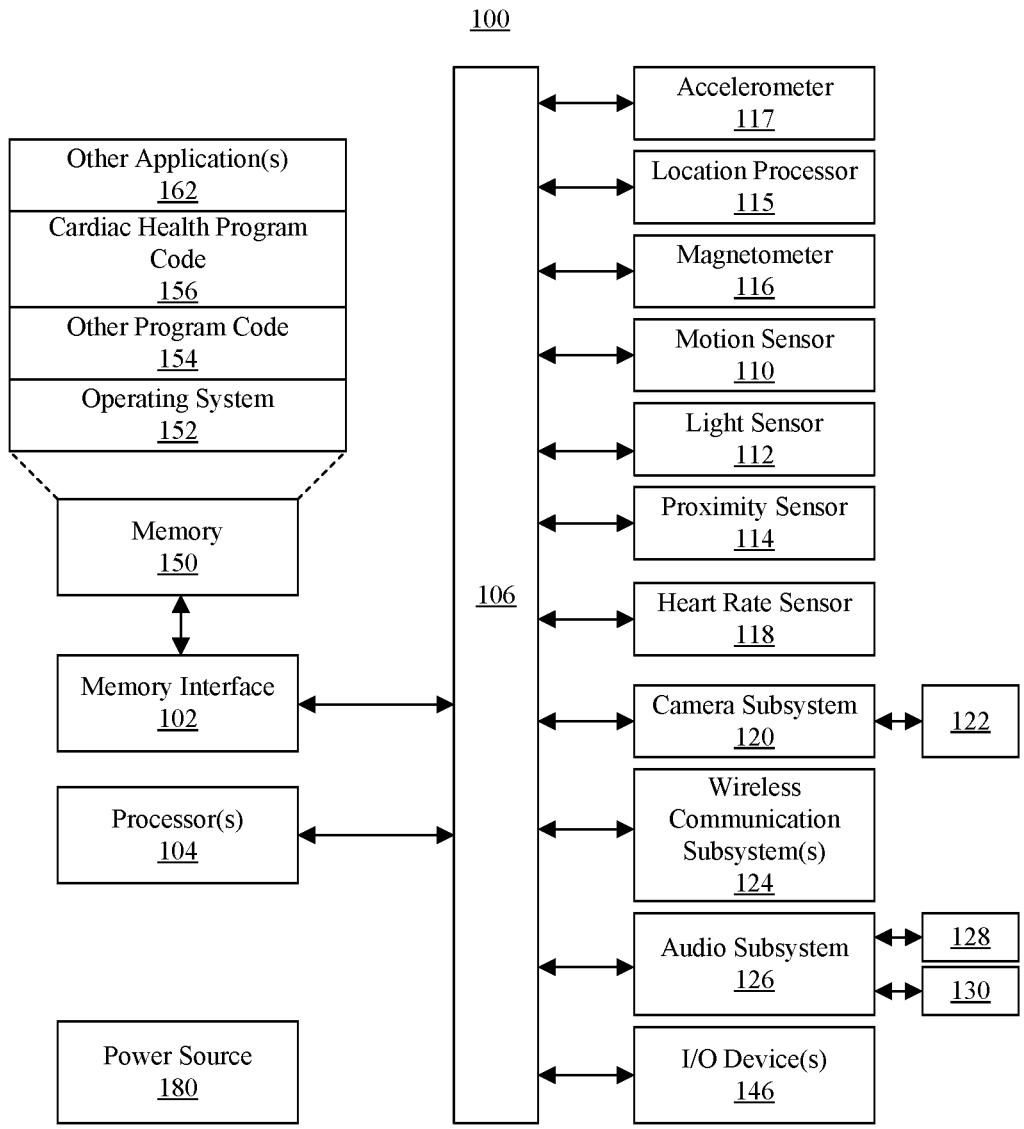
FIG. 1 illustrates an example architecture for a device.

While the disclosure concludes with claims defining novel features, it is believed that the various features described herein will be better understood from a consideration of the description in conjunction with the drawings. The process(es), machine(s), manufacture(s) and any variations thereof described within this disclosure are provided for purposes of illustration. Any specific structural and functional details described are not to be interpreted as limiting, but merely as a basis for the claims and as a representative basis for teaching one skilled in the art to variously employ the features described in virtually any appropriately detailed structure. Further, the terms and phrases used within this disclosure are not intended to be limiting, but rather to provide an understandable description of the features described.

This disclosure relates to detecting cardiac disease within individuals and, more particularly, to detecting chronotropic incompetence or "CI." In view of the significant effect CI may have upon cardiac mortality, accurate and timely detection of CI is of utmost importance. With accurate and timely detection of CI, medical care providers may be alerted to an individual's condition. Suitable medical intervention may then be initiated for the individual such as addressing CI through a rehabilitation program or the like.

Accordingly, one or more embodiments described within this disclosure relate to apparatus such as a device and/or system capable of detecting CI, method(s) of detecting CI, and computer readable storage media implementing the various methods described herein. The apparatus is capable of using an estimate of activity level for an individual to determine a baseline cardiac health measure, e.g., a baseline heart rate (HR) for the individual. The apparatus is further capable of analyzing sensor data for the individual to validate the estimate of activity level. Validation allows the apparatus to ensure the accuracy of what is a subjective determination on the part of the individual. The apparatus is further capable of determining a cardiac health measure, e.g., HR, for the individual from the sensor data and performing a comparison of the cardiac health measure rate from the sensor data to the baseline cardiac health measure to detect CI in the individual.

In one or more other embodiments, the apparatus is capable of accounting for one or more confounders. A confounder is a confounding variable or a confounding factor in an unambiguous determination of whether an individual has CI. Examples of confounders include, but are not limited to, any of a variety of behaviors, medical conditions, or other data items that define a context for the individual. More specific examples of confounders can include, but are not limited to, stress, fatigue, sleep disorder(s) or disturbances, medications being taken, medication regimen, or other pathological conditions that would affect the normal response of heart rate to physical exertion.

One or more of the embodiments described within this disclosure may be used or incorporated into various rehabilitation programs. For example, the rehabilitation program may be a cardiac rehabilitation program. As an illustrative example, upon intake of an individual into a rehabilitation program, one or more baselines for the individual can be established. The baseline(s) may include information relating to health of the individual and, in particular, cardiac health of the individual. The baseline(s) may be determined as the individual performs various exercises, performs day-to-day activities, etc. while undergoing evaluation. The baseline(s) may be used to ascertain general levels of cardiac fitness and/or for determining whether the individual has CI. In generating the baseline(s), validation factors may be included therewith to aid in accurately assessing whether the individual has CI.

Further aspects and details of the inventive arrangements are described below with reference to the figures. For purposes of simplicity and clarity of illustration, elements shown in the figures have not necessarily been drawn to scale. For example, the dimensions of some of the elements may be exaggerated relative to other elements for clarity. Further, where considered appropriate, reference numbers are repeated among the figures to indicate corresponding, analogous, or like features. In addition, it should be appreciated that while cardiac rehabilitation is provided for purposes of illustration throughout this document, the examples provided herein are not intended to be limiting of the inventive arrangements described.

FIG. 1 illustrates an example architecture 100 for a device. Architecture 100 can include a memory interface 102, one or more processors 104 (e.g., image processors, digital signal processors, data processors, etc.), and an interface 106. Memory interface 102, processor(s) 104, and/or interface 106 can be separate components or can be integrated in one or more integrated circuits. The various components in architecture 100, for example, can be coupled by one or more communication buses or signal lines (e.g., interconnects and/or wires).

Sensors, devices, subsystems, and input/output (I/O) devices can be coupled to interface 106 to facilitate the functions and/or operations described herein including the generation of sensor data. The various sensors, devices, subsystems, and/or I/O devices may be coupled to interface 106 directly or through one or more intervening I/O controllers (not shown).

For example, motion sensor 110, light sensor 112, and proximity sensor 114 can be coupled to interface 106 to facilitate orientation, lighting, and proximity functions of a device using architecture 100. Location processor 115 (e.g., a GPS receiver) can be connected to interface 106 to provide geo-positioning sensor data. Electronic magnetometer 116 (e.g., an integrated circuit chip) can also be connected to interface 106 to provide sensor data that can be used to determine the direction of magnetic North. Thus, electronic magnetometer 116 can be used as an electronic compass. Accelerometer 117 can also be connected to interface 106 to provide sensor data that can be used to determine change of speed and direction of movement of a device in 3-dimensions using architecture 100. Heart rate sensor 118 can be connected to interface 106 to generate sensor data and facilitate measurement of a heartbeat and the determination of a heart rate.

Camera subsystem 120 can be coupled to an optical sensor 122. Optical sensor 122 can be implemented as a charged coupled device (CCD), a complementary metal-oxide semiconductor (CMOS) optical sensor, etc. Camera subsystem 120 and optical sensor 122 can be used to facilitate camera functions, such as recording images and video clips (hereafter "image data"). For purposes of this disclosure, image data is a subset of sensor data.

Communication functions can be facilitated through one or more wireless communication subsystems 124, which can include radio frequency receivers and transmitters and/or optical (e.g., infrared) receivers and transmitters. The specific design and implementation of communication subsystem 124 can depend on the communication network(s) over which a device using architecture 100 is intended to operate. For example, wireless communication subsystem(s) 124 may be designed to operate over a GSM network, a GPRS network, an EDGE network, a WiFi or WiMax network, a Bluetooth network, and/or any combination of the foregoing. Wireless communication subsystem(s) 124 can include hosting protocols such that a device using architecture 100 can be configured as a base station for other wireless devices.

Audio subsystem 126 can be coupled to a speaker 128 and a microphone 130 to facilitate voice-enabled functions, such as voice recognition, voice replication, digital recording, and telephony functions. Audio subsystem 126 is capable of generating audio type sensor data.

I/O devices 146 can be coupled to interface 106. Examples of I/O devices 146 can include, but are not limited to, display devices, touch sensitive display devices, track pads, keyboards, pointing devices, communication ports (e.g., USB ports), buttons or other physical controls, and so forth. A touch sensitive device such as a display screen and/or a pad is configured to detect contact, movement, breaks in contact, etc., using any of a variety of touch sensitivity technologies. Example touch sensitive technologies include, but are not limited to, capacitive, resistive, infrared, and surface acoustic wave technologies, as well as other proximity sensor arrays or other elements for determining one or more points of contact with a touch sensitive device. One or more of I/O devices 146 may be adapted to control functions of sensors, subsystems, and such of architecture 100.

Architecture 100 further includes a power source 180. Power source 180 is capable of providing electrical power to the various elements of architecture 100. In one embodiment, power source 180 is implemented as one or more batteries. The batteries may be implemented using any of a variety of different battery technologies whether disposable (e.g., replaceable) or rechargeable. In another embodiment, power source 180 is configured to obtain electrical power from an external source and provide power (e.g., DC power) to the elements of architecture 100. In the case of a rechargeable battery, power source 180 further may include circuitry that is capable of charging the battery or batteries when coupled to an external power source.

Memory interface 102 can be coupled to memory 150. Memory 150 can include high-speed random access memory (e.g., volatile memory) and/or non-volatile memory, such as one or more magnetic disk storage devices, one or more optical storage devices, and/or flash memory (e.g., NAND, NOR). Memory 150 can store operating system 152, such as LINUX, UNIX, a mobile operating system, an embedded operating system, etc. Operating system 152 may include instructions for handling basic system services and for performing hardware dependent tasks.

Memory 150 may also store other program code 154 such as communication instructions to facilitate communicating with one or more additional devices, one or more computers and/or one or more servers; graphical user interface instructions to facilitate graphic user interface processing; sensor processing instructions to facilitate sensor-related processing and functions; phone instructions to facilitate phone-related processes and functions; electronic messaging instructions to facilitate electronic-messaging related processes and functions; Web browsing instructions to facilitate Web browsing-related processes and functions; media processing instructions to facilitate media processing-related processes and functions; GPS/Navigation instructions to facilitate GPS and navigation-related processes and functions; security instructions to facilitate security functions; camera instructions to facilitate camera-related processes and functions including Web camera and/or Web video functions; and so forth. Memory 150 may also store one or more other application(s) 162.

Memory 150 may store cardiac health program code 156 to facilitate detection of cardiac disease such as CI within users. Cardiac health program code 156 is capable of analyzing sensor data, querying a user for input such as an estimate of activity level, and performing comparisons of sensor data and/or user input with baseline information. Further aspects of operations performed through execution of cardiac health program code 156 are described herein with reference to the remaining figures. Memory 150 may also store various types of data (not shown) such as sensor data and/or data obtained by way of received user input(s).

Each of the above identified instructions and applications can correspond to a set of instructions for performing one or more functions described above. These instructions may or may not implemented as separate software programs, procedures, or modules. Memory 150 can include additional instructions or fewer instructions. Furthermore, various functions of architecture 100 may be implemented in hardware and/or in software, including in one or more signal processing and/or application specific integrated circuits.

Program code stored within memory 150 and any data items used, generated, and/or operated upon by a device utilizing an architecture the same as or similar to that of architecture 100 are functional data structures that impart functionality when employed as part of the device. Further examples of functional data structures include, but are not limited to, sensor data, data obtained via user input, baselines, and so forth. As defined within this disclosure, a "data structure" is a physical implementation of a data model's organization of data within a physical memory. As such, a data structure is formed of specific electrical or magnetic structural elements in a memory. A data structure imposes physical organization on the data stored in the memory as used by an application program executed using a processor.

In one or more other embodiments, one or more of the various sensors and/or subsystems described with reference to architecture 100 may be separate devices that are coupled or communicatively linked to architecture 100 through wired or wireless connections. For example, one or more or all of accelerometer 117, location processor 115, magnetometer 116, motion sensor 110, light sensor 112, proximity sensor 114, camera subsystem 120, audio subsystem, heart rate sensor 118, and so forth may be implemented as separate systems or subsystems that couple to processor 104, memory interface 102, and/or interface 106 via a wired or wireless connection(s). In some embodiments, such sensors and/or subsystems are configured to generate sensor data that is stored in a memory external to architecture 100. In that case, architecture 100, e.g., processors 104, may access the sensor data for use and/or analysis as described herein.

Architecture 100 may include fewer components than shown or additional components not illustrated in FIG. 1 depending upon the particular type of device that is implemented. In addition, the particular operating system and/or application(s) and/or other program code included may also vary according to device type. Further, one or more of the illustrative components may be incorporated into, or otherwise form a portion of, another component. For example, a processor may include at least some memory.

While a device configured to perform the operations described herein may utilize architecture 100, architecture 100 is provided for purposes of illustration and not limitation. A device configured to perform the operations described herein may have a different architecture than illustrated in FIG. 1. The architecture may be a simplified version of architecture 100 and include a processor and memory storing instructions. The architecture may include one or more sensors as described herein. A device using architecture 100 or an architecture similar thereto is capable of collecting data using the various sensors of the device or sensors coupled thereto. Within this disclosure, data generated by a sensor is called "sensor data."

Examples of devices that may utilize architecture 100 or another computing architecture as described for detecting CI may include, but are to limited to, a smart phone or other mobile device, a wearable computing device (e.g., smart watch, fitness tracker, patch, etc.), a dedicated medical device, a computer (e.g., desktop, laptop, tablet computer, other data processing system, etc.), and any suitable electronic device capable of sensing and processing the sensor data. Furthermore, it will be appreciated that embodiments can be deployed as a standalone device or deployed as multiple devices in a distributed client-server networked system.

Figure 2:
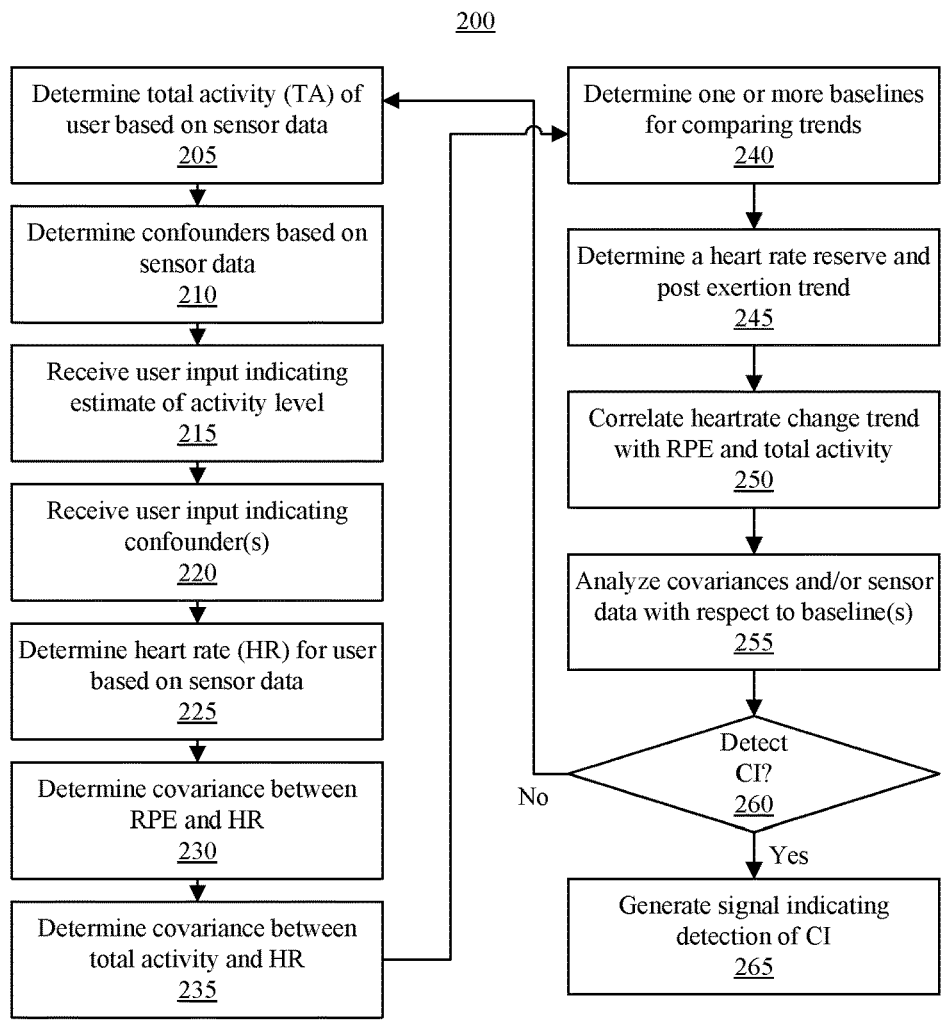
FIG. 2 illustrates an example method of detecting chronotropic incompetence (CI).

FIG. 2 illustrates an example method 200 of detecting CI. Method 200 may be performed by a device or system having an architecture as described within this disclosure. Method 200 may begin in a state where sensor data has been collected for the user over time, e.g., a period of time, and is available for analysis. In one or more embodiments, the device collects the sensor data. In one or more other embodiments, one or more items of sensor data or all of the sensor data may be generated from other system(s) and/or device(s) and be read and/or processed by the device performing method 200.

In block 205, the device determines the total activity or "TA" of a user based on sensor data. The device is capable of determining the total activity for the user using accelerometer data. In one example, the device is capable of determining the total activity for the user based on the power of the accelerometer output.

In block 210, the device optionally determines one or more confounders based on sensor data. A more detailed description of confounders and the automatic detection of such confounders by the device is provided herein in connection with FIG. 4.

In block 215, the device optionally receives a user input indicating an estimate of activity level for the user. In one or more embodiments, the estimate of the user's activity level is a rating of perceived exertion or RPE. RPE is a measure of physical activity intensity level. RPE is based upon somatic or psychosomatic sensations related to difficulty of exertion that a user experiences during physical activity which lead to symptoms such as increased heart rate, increased perspiration or breathing rate, increased sweating, muscle fatigue, and so forth. In any event, the RPE is generally considered a subjective measure of exertion on the part of the user at least when received as a user input in response to querying the user. The device is capable of receiving a user input specifying an RPE value.

In one or more embodiments, the RPE is expressed using the Borg scale. Table 1 below illustrates the scoring of RPE on the Borg scale.

TABLE 1

| Number | Level of Exertion |
|--------|-------------------|
| 6      |                   |
| 7      | Very, Very Light  |
| 8      |                   |
| 9      | Very Light        |
| 10     |                   |
| 11     | Fairly Light      |
| 12     |                   |
| 13     | Somewhat hard     |
| 14     |                   |
| 15     | Hard              |
| 16     |                   |
| 17     | Very Hard         |
| 18     |                   |
| 19     | Very, Very Hard   |
| 20     |                   |

In one or more other embodiments, a different scale for measuring RPE may be used. In this regard, the inventive arrangements are not intended to be limited to using one particular scale for RPE. It should be appreciated that in an effort to ensure consistent results, users may be trained in estimating activity level using an appropriate scale. For example, within a hospital setting, in a rehabilitation setting, or anywhere working with trained medical staff, the user may be instructed in how to properly estimate activity level using the selected scale.

In one or more other embodiments, the estimate of activity level may be determined in an automated manner by the device without querying the user for such information. In that case, querying the user for an estimate of activity level need not be performed. The device can be adapted to determine an estimate of activity level, e.g., an RPE, from sensor data. In one example, the device is capable of determining or estimating activity level such as RPE by detecting respiration (ventilation) related sound from the user related to exertion from audio sensor data. The device may estimate activity level or RPE by comparing progressive changes in the respiratory related sounds of the user from audio sensor data that are indicative of exertion. Detecting respiratory sound is described herein in greater detail with reference to FIG. 3.

In block 220, the device optionally receives a user input indicating one or more confounders. The device, for example, may query the user for a list of confounders or to select those confounders applicable to the user from a list of confounders presented to the user. For example, the device may query the user about medication intake. In one example, the device queries or asks the user whether the user is taking any beta blocker medication or any other drug that changes chronotropic nature of the function of the heart. Such medications and/or drugs may affect the measurements described below. As such, depending upon the medication and/or drugs indicated, the threshold for determining CI may be adjusted or changed.

In block 225, the device determines a heart rate (HR) for the user based upon the sensor data. In block 230, the device determines a covariance COV(RPE, HR) between RPE and the HR. In block 235, the device determines a covariance COV(TA, HR) between the measured TA from block 205 and the HR of block 225. For example, referring to blocks 230 and 235, the device is capable of calculating covariances between any pair of the following: an HR time series, a TA time series, and RPE.

In block 240, the device determines one or more baseline cardiac health measures for comparing trends. In one or more embodiments, baseline cardiac health measures (or baselines) may be determined with the user at rest and/or for one or more or each of the possible RPE values. The baselines may be stored for subsequent comparison with newly collected sensor data and/or user input. Example baselines include, but are not limited to:

a covariance $COV(RPE_{Rest}, HR_{Rest})$ between $RPE_{Rest}$ and $HR_{Rest}$;

a covariance between RPE and HR during exertion which can be denoted by $COV(RPE_{exertion}, HR_{exertion})$;

a covariance $COV(HR_{Rest}, TA_{Rest})$ between $HR_{Rest}$ and $TA_{Rest}$ at rest;

a covariance $COV(HRR, HR_D)$ between HRR (heart rate recovery) and $HR_D$, where subscript "D" indicates deceleration trend (post-exertion) for HR with effort level and with total activity level as measured by sensors;

a covariance COV(EEE, RPE) between EEE (exercise energy expended), as may be measured using accelerometer activity, and RPE; and/or a respiration related sound recorded or observed at different RPE levels.

In one or more embodiments, a baseline cardiac health measure is determined from sensor data as described within this disclosure. For example, baseline cardiac health measures may be determined while the user is at rest or in a known state. In one or more other embodiments, a baseline cardiac health measure is a reference state or data, e.g., predetermined or fixed data, that is specified by a physician, obtained from a standard, or the like and used for purposes of comparison as described herein.

In block 245, the device optionally determines an HRR and the HRR trend post-exertion. The device further is capable of correlating the HR change trend (e.g., the deceleration trend) with the RPE and with the measured TA of block 205. In one aspect, the device is capable of determining whether the heart rate recovery has a bi-exponential trend. For example, the device is capable of examining the logarithm of HRR for bi-exponentiality. The absence of a bi-exponential trend indicates CI. In block 250, the device optionally correlates HR change trend with RPE and total activity.

In block 255, the device is capable of analyzing one or more of the determined covariances and/or sensor data with respect to baselines. For example, the device is capable of detecting an anomaly such as a difference by more than a threshold from the baseline or an expected value. The lack of an expected covariance suggests detection of CI. In one embodiment, the device is capable of determining that an individual has CI responsive to determining that the covariance between energy expanded and RPE remains the same with the HR not being elevated. In other cases, where the covariance between EEE and RPE remains the same with EEE being low and RPE being high, the device is capable of determining that the individual has a reduced fitness level (e.g., not CI). The device is capable of calculating a cardiac health measure, including any of the covariances described herein, from sensor data to compare with a baseline cardiac health measure (e.g., a baseline covariance) to determine or estimate whether the user has CI.

In one or more embodiments, the threshold for CI is adjusted based upon medication intake or other confounders as determined in block 220. In one or more other embodiments, the threshold for CI is adjusted based upon one or more confounders detected within the sensor data from block 210. Examples of confounders include, but are not limited to, stress; sleep deprivation; tiredness; depression (mood); consumption of stimulants (caffeine, intoxicants etc.); any other drug that may have an effect on blood pressure and/or HR; state of health including fever, dehydration, or any other condition where HR and/or blood pressure, or other Autonomic Nervous System (ANS) markers can be reasonably expected to undergo significant change; and so forth. In one or more embodiments, the threshold for detecting CI is adjusted upward or downward based upon whether one or more of the confounders are detected within the sensor data. Confounders and the automated detection thereof from sensor data are discussed in further detail in connection with FIG. 4.

In one or more embodiments, the device is capable of accounting for confounders by computing the Relative Increase in HR (RIHR). RIHR is also called Increment % from HR at rest to Peak HR. RIHR may be calculated using the expression [(Peak HR−HR at Rest)/(HR at Rest)]×100.

In some cases, for individuals with CI that are taking beta blockers, a modified HR reserve may be used to account for confounders. The modified HR reserve (MHRR) may be calculated using the expression [(Increment % from HR at rest to peak HR)/(220−Age−HR at rest)]×100. Typically, HR reserve is calculated using the expression [(Peak HR−HR at rest)/(220−Age−HR at rest)]×100. The device further is capable of computing MHRR in one or more embodiments. It should be appreciated that HR reserve can also be calculated by estimating the Peak HR via any other varieties of accepted formulas that correlate expected peak HR with a person's age.

Using either RIHR or MHRR moves from an absolute calculation to a relative calculation for instances where HR may be depressed due to confounders. These relative calculations facilitate accurate detection of CI in instances where the HR increase is supposed to be larger if the HR at rest in the RIHR and/or MHRR expressions is modified to reflect or imply a baseline HR for a given instance. The device, for example, may calculate a baseline HR (e.g., the HR at rest) by measuring HR for an appropriate period of rest preceding the given exercise at a reasonably close time interval.

Using the RIHR and/or MHRR, CI detection may be performed subject to any confounders. It should be appreciated that the techniques described herein may be further modified to account for one or more confounders responsive to determining an approximation of the impact the confounder may have. For example, if the HR of an individual is typically elevated by 5 beats per minute (BPM) after caffeine consumption, then even without determining the baseline HR for a given instance, the HR may be selected from historical data. The device is capable of adding the 5 BPM to the historical HR to account for the caffeine consumption.

In block 260, the device determines whether one or more indicators of CI are detected. If so, method 200 proceeds to block 265. If not, method 200 may loop back to block 205 to continue processing. In block 265, the device generates a signal or notification that is output indicating that CI is detected. In one or more embodiments, responsive to detecting CI, the device is capable of providing an indication to a remote system. For example, the device is capable of providing a message or indication to a healthcare provider server based on the computed information.

While the above description is described in the context of computing covariance, alternative embodiments can use other similarity measures or dissimilarity measures, such as correlation or distance functions. Further, one or more or each of the calculations described in connection with FIG. 2 can be contextual. For example, the CI of a user may be different in morning vs. in evening due to the circadian rhythm of various hormones secreted by the user's endocrine system. In this regard, the CI threshold that is used may be varied according to context such as morning vs. evening.

Figure 3:
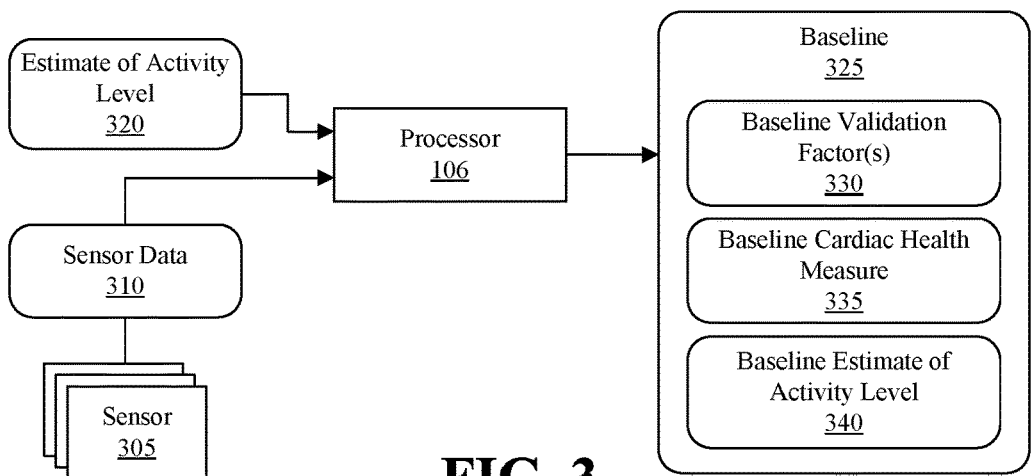
FIG. 3 illustrates an example of baseline generation for CI detection.

FIG. 3 illustrates an example of baseline generation for CI detection. Baseline generation may be performed at any of a variety of different times in order to establish one or more baselines for purposes of detecting CI in a user. In one or more embodiments, baseline generation may be performed as part of an intake or onboarding process of a rehabilitation program. For example, a user may be asked to perform one or more tasks, activities, or exercises. During that time, baseline 325 may be generated or otherwise determined. The baselines determined may be stored in the user's device for purposes of later comparison.

As shown, one or more sensors 305 are capable of generating sensor data 310. Example sensors 305, as discussed with reference to FIG. 1, include, but are not limited to, an accelerometer, a heart rate sensor, a microphone, and so forth. Sensor data 310 is generated over a period of time. Accordingly, for the various values and/or quantities described, it should be appreciated that sensor data 310 includes a time series of such data. Sensor data 310 may be stored in a memory (not shown). As such, processor 106 may access (read and/or write) sensor data 310.

Processor 106 is also capable of receiving an estimate of activity level (EAL) 320 for the user. EAL 320 may be provided by way of a received user input. As noted, a device may query a user for EAL 320. In another aspect, EAL 320 may be entered by the user or an administrator responsive to asking the user. As discussed, in one or more embodiments, EAL 320 is a rating of perceived exertion or RPE.

Processor 106 is capable of operating on sensor data 310 and EAL 320 to generate a baseline 325. In the example of FIG. 3, baseline 325 includes a baseline cardiac health measure 335 and baseline EAL 340. Processor 106 is capable of determining a cardiac health measure for the user from sensor data 310 as generated by a sensor at or about the time that EAL 320 is received. Processor 106 stores the determined cardiac health measure as baseline cardiac health measure 335 in association with EAL 320 as part of baseline 325. EAL 320, when stored as part of baseline 325, is referred to as the "baseline EAL" 340.

In one or more embodiments, the baseline cardiac health measure is HR. In one or more other embodiments, the baseline cardiac health measure is one or more of the covariances described herein. In one or more other embodiments, the baseline cardiac health measure is one or more or a combination of HR and one or more of the covariances.

In one or more embodiments, processor 106 is capable of determining one or more baseline validation factors 330 from sensor data 310 for the time period within sensor data 310 for which baseline HR 335 is determined. A "validation factor," as defined herein, for example, is one or more items of data determined from sensor data 310 other than items of sensor data used to determine baseline cardiac health measure 335, that is used to validate an EAL received from the user. Appreciably, the time and/or time period for which a baseline validation factor 330 is determined for baseline 325 is the same time and/or time period for which baseline HR 335 and baseline EAL 340 are determined for baseline 325.

One example of a validation factor, including a baseline validation factor, is TA. TA, which indicates energy expended by the user, can be measured by accelerometer data that is included in sensor data 310. TA may be determined as previously described herein with reference to FIG. 2, for example. Processor 106 operates on accelerometer data to measure the energy expended, e.g., an amount of work for a given time or period of time, performed by the user. In one or more embodiments, processor 106 is configured to include or read additional attributes of the user such as height, weight, and age in order to more accurately calculate the expended energy of the user as a baseline validation factor 330.

Another example of a validation factor, including a baseline validation factor, is respiratory sound indicating exertion. The respiratory sound may indicate a level of exertion for a user indicating a level of difficulty. The microphone generates audio data that is included in sensor data 310. Processor 106 operates on the audio data to measure respiratory indications for exertion for a given time or period of time, for the user. For example, processor 106 is capable of detecting breathing sounds (e.g., breath, wheezing, coughing, etc.) within the audio data and determining the characteristics of the breathing sounds as a baseline validation factor 330. The respiratory sound may be analyzed for different RPE to determine baselines for the different RPE.

Accordingly, baseline validation factor(s) 330 may be stored with baseline cardiac health measure 335 and baseline EAL 340 within baseline 325. By storing baseline validation factor(s) 330 as part of baseline 325, when baseline 325 is later used for purposes of evaluating cardiac health of the user, newly determined validation factors may be compared with baseline validation factors 330 for a given EAL and/or cardiac health measure. The validation process is described in greater detail with reference to FIG. 4.

In the example of FIG. 3, while one baseline is illustrated, it should be appreciated that the operations described may be performed one or more additional times in order to generate further baselines. In one example, a baseline may be generated for one or more or for each possible value of the estimate of activity level or RPE. Referring to Table 1, for example, a baseline may be generated for each possible score for the RPE from 6 to 20.

Figure 4:
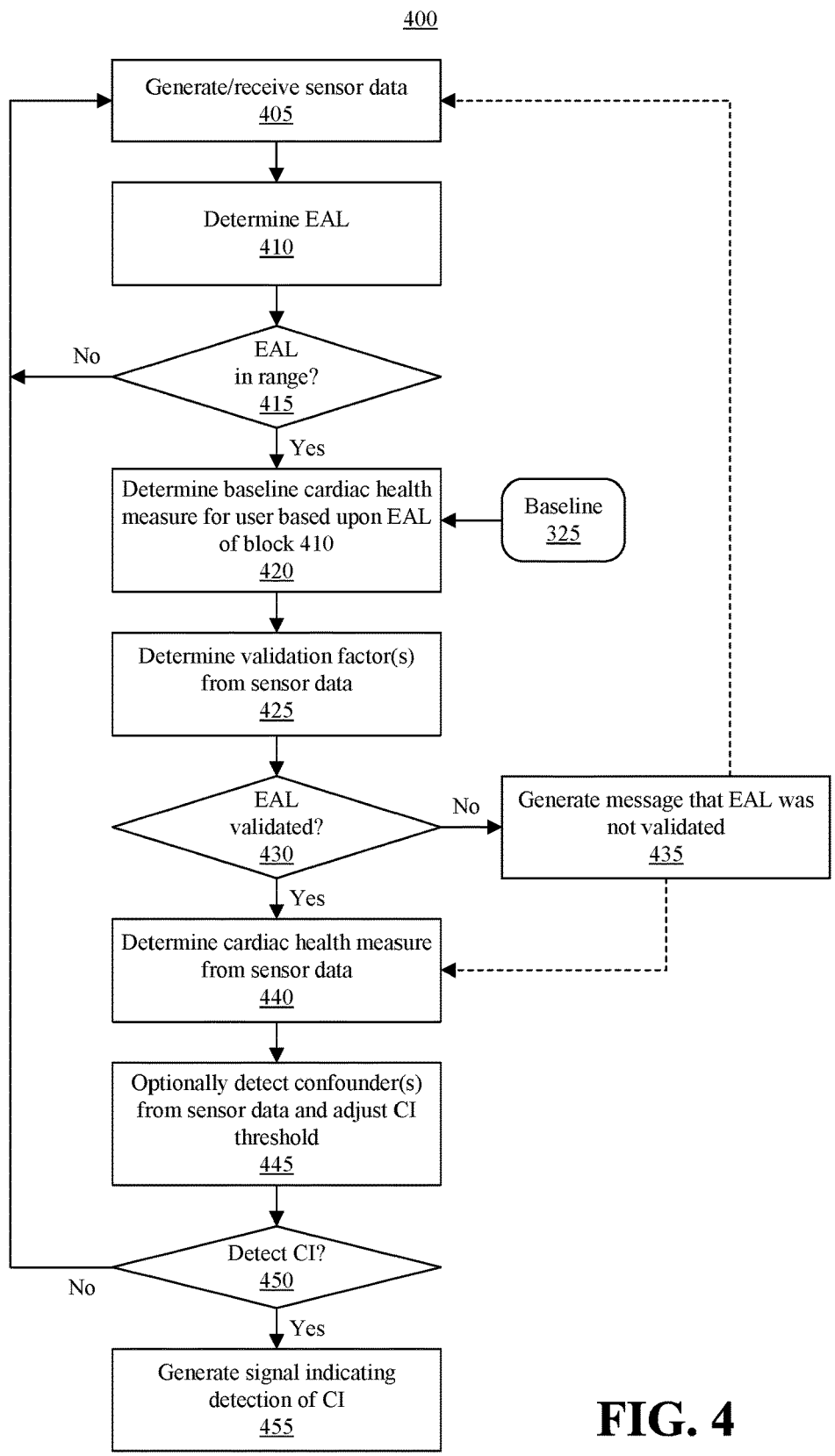
FIG. 4 illustrates another example method of detecting CI.

FIG. 4 illustrates is another example method 400 of detecting CI. Method 400 may be performed by a device or system having a computing architecture as described within this disclosure. Method 400 may begin in a state where one or more baselines as described herein with reference to FIGS. 2 and 3 are generated and stored. The baselines are available for use by the device in detecting CI.

In block 405, the device generates or receives sensor data. As noted, in one or more embodiments, the device collects the sensor data. In one or more other embodiments, one or more items of sensor data or all of the sensor data may be generated from other system(s) and/or device(s) and be read or received by the device performing method 400. In block 410, the device determines an EAL. In one or more embodiments, the device queries the user for an EAL. The device receives a user input specifying the EAL. In one or more other embodiments, the device is capable of estimating an EAL based upon respiratory sounds as previously described.

In block 415, the device determines whether the EAL is in a defined range. If so, method 400 continues to block 420. If not, method 400 loops back to block 405 to continue processing. In one or more embodiments, the EAL must be within a particular range in order to detect CI. In one example, the range is an RPE of 13 or 14. In that case, if the EAL specifies an RPE of 13 or 14, method 400 continues to block 420. If not, method 400 loops back to block 405 to continue processing.

In block 420, the device determines the baseline cardiac health measure for the user based upon the EAL determined in block 410. For example, the device uses the EAL determined in block 410 and locates a matching baseline EAL within the baselines. As discussed with reference to FIG. 3, for example, each baseline stores a baseline EAL. If, for example, the EAL of block 410 is an RPE value of 13, the device looks up the baseline having a baseline EAL with an RPE value of 13. If, for example, the EAL of block 410 is an RPE value of 14, the device looks up the baseline having a baseline EAL with an RPE value of 13. For purposes of discussion, the device is capable of looking up baseline 325 using the EAL determined in block 410 as the baseline EAL and determining the baseline cardiac health measure from baseline 325. As noted, in one or more embodiments, the baseline cardiac health measure is HR, but may be or include one or more of the covariances described.

In block 425, the device is capable of determining one or more validation factors from the sensor data. The validation factors may be determined for the same time and/or same period of time to which the EAL determined in block 410 corresponds. For example, the device is capable of determining the validation factor of activity level from accelerometer sensor data and/or characteristics of respiratory sound indicating exertion from audio sensor data.

In block 430, the device is capable of validating the EAL received in block 410. In one or more embodiments, the device validates the EAL of block 410 by comparing one or more of the validation factors determined in block 425 with the corresponding baseline validation factor(s), e.g., validation factor(s) of the same type, from the baseline used to determine the baseline cardiac health measure. For example, the device may compare one or more of the validation factors determined in block 425 using current sensor data with the stored baseline validation factor(s) 330 of baseline 325.

As an illustrative example, the device may validate the EAL of block 410 by determining that the characteristics of respiratory sound indicating exertion determined in block 425 are within a predetermined threshold of, or match, baseline characteristics of respiratory sound indicating exertion specified in baseline validation factor(s) 330. As another illustrative example, the device may validate the EAL of block 410 by determining that the TA determined in block 425 is within a predetermined threshold or amount of a baseline TA specified in baseline validation factor(s) 330.

In still another illustrative example, the device may validate the EAL of block 410 by determining that the characteristics of respiratory sound determined in block 425 is/are the same as or similar to the characteristics of respiratory sound specified in baseline validation factor(s) 330 and that the total activity determined in block 425 is within a predetermined threshold or amount of a baseline total activity specified in baseline validation factor(s) 330.

In one or more embodiments, where the EAL is determined automatically from respiratory sound, the device may utilize a validation factor other than respiratory sound to perform validation.

Block 430 ensures that the EAL provided by the user is consistent. In the event that the user begins to provide inconsistent EALs, one or more of the validation factors will likely mismatch the baseline validation factors. For example, in the case where the user over estimates the EAL, the validation factors will likely be lower than the baseline validation factors obtained from baseline 325, e.g., lower than the predetermined threshold or amount.

In any case, if the EAL is validated, method 400 may continue to block 440. If the EAL is not validated, method 400 may proceed to block 435. In block 435, the device may generate a message or notification that the EAL was not validated or that validation was not successful. In one or more embodiments, after block 435, method 400 may loop back to block 405 to continue processing. In one or more other embodiments, after block 435, method 400 may continue to block 440. For example, method 400 may continue to block 440 to detect CI despite the unsuccessful validation of the EAL. In that case, where CI is detected, the signal indicating detection of CI in block 455 may further indicate that while CI is detected, validation of the EAL was unsuccessful.

In block 440, the device is capable of determining a cardiac health measure for the user from the sensor data. In one embodiment, the cardiac health measure is HR. The device is capable of determining the HR for the user from the sensor data for the same time or same time period as the EAL received in block 420. In one or more other embodiments, the cardiac health measure is one or more covariances and/or a combination of HR and one or more covariances.

In block 445, the device optionally detects one or more confounders from the sensor data and adjusts a CI threshold. In one or more embodiments, the device is capable of detecting one or more confounders from the sensor data. Responsive to detecting a confounder in the sensor data, the device adjusts the CI threshold. In one or more embodiments, the CI threshold specifies how far the user's HR, as determined in block 440, must be from a baseline HR (e.g., the baseline cardiac health measure) of block 420 for the device to detect CI. The CI threshold may be expressed as a percentage, a predetermined amount, or the like.

In one example, the device is capable of detecting, from the sensor data, the confounder of sleep deprivation. For example, the device is capable of measuring sleep of the user using HR data and accelerometer data. The device is capable of determining the amount of time that the user sleeps and comparing the amount of time spent sleeping with a baseline amount of time (whether personal to the user or a generalized baseline determined across one or more other users) to determine sleep deprivation for the user. The device is capable of determining a measure of sleep deprivation expressed as a confounding factor.

In another example, the device is capable of detecting, from the sensor data, the confounder of stress. When under stress, for example, the user's ANS arousal and valence are typically in the second quadrant of the Circumplex Model of Emotions, which can be determined by HR and HR variability (HRV) analysis where both trend down at the same time. In one embodiment, the device is capable of using HR and/or HRV to determine whether the user is under stress and/or the amount of stress. For example, the device is capable of determining whether the user is subject to stress and whether the amount of stress exceeds a baseline amount of stress based upon HR (e.g., energy) and HRV (e.g., mood) of the user both being low (e.g., below a baseline for HR and/or a baseline for HRV) at the same time and/or remaining low (concurrently) for at least a minimum amount of time. The baseline may be specific to the user or generalized across one or more different users. Responsive to determining that the HR and HRV both are low for at least the minimum amount of time, for example, the device determines that the user is experiencing stress. A measure of stress may be expressed as a confounding factor.

Responsive to detecting one or more of the confounding factors, the device adjusts the CI threshold. For example, the device increases the CI threshold. In one or more embodiments, the device increases the CI threshold a predetermined amount or percentage for each confounder detected. The device is further capable of increasing the CI threshold based upon the amount of one or more or each of the confounders detected. In one or more other embodiments, the device increases the CI threshold only responsive to determining that the, or each, confounder, while detected for the time or time period corresponding to the EAL received in block 410, was not present for the determination of the baseline HR.

In one or more other embodiments, the device is capable of using recent exertion history of the user into account. As an illustrative example, if the user has endured significant exertion in comparison to the user's baseline level of exertion in a preceding time period that is sufficiently close to the time period being evaluated for CI, the user is likely tired.

As such, the user is likely to indicate a high RPE despite the effort level for that given instance or period of time not really being high. Thus, in one or more embodiments, the device is capable of excluding instances of higher than baseline level of exertion that occur within a threshold or predetermined amount of time of an earlier period or instance of higher than baseline level of exertion from consideration in CI detection.

In block 450, the device determines whether CI is detected for the user. In one or more embodiments, the device compares the HR determined in block 440 with the baseline HR determined in block 420. The device is capable of determining whether the HR is within the CI threshold of the baseline HR. In one example, the CI threshold is 80% of the baseline HR. If the HR is within the threshold or predetermined amount of the baseline HR, the device does not detect CI for the user. Accordingly, method 400 may loop back to block 405. If the HR is not within the threshold or predetermined amount of the baseline HR, the device detects CI for the user. In that case, method 400 continues to block 455.

In some cases, the device is configured to adjust the CI threshold. In one or more embodiments, the device is capable of measuring fraction of HR reserve achieved after exercise. In that case, where the user is starting with a higher HR than the user's HR at rest, rather than using HR at rest, the device may compute the fraction of HR increase achieved by using the HR (during an inactive period) immediately prior to the period of exercise.

In other cases, the HR increase experienced by a user may be affected by stress, a medical condition, and/or a medication. These effects may be determined by using a circadian baseline of the user that is annotated with events and times. The circadian baseline, for example, may indicate events such as ingestion of caffeine and/or medication and times. Stress may be detected automatically. In one or more embodiments, the device is capable of receiving data indicating stress, medical condition, and/or medication from a medical provider and/or medical provider system.

In block 455, the device generates a signal or notification that is output indicating that CI is detected. In one or more embodiments, responsive to detecting CI, the device is capable of providing an indication to a remote system. For example, the device is capable of providing a message or indication to a healthcare provider server based on the computed information.

Referring to FIGS. 2 and 4, based upon the above calculations such as the presence and/or lack of covariance and/or the comparisons described, the device is capable of not only detecting CI, but also of detecting or determining improvement in CI. Improvement in CI can be a significant marker of improved health, and reduced mortality and morbidity. Conversely, worsening CI can imply a greater risk of mortality and morbidity and thus requires additional and appropriate clinical attention from the caretaking staff.

In one or more other embodiments, additional sensors may be incorporated to provide measurements that, if available, may be used as validation factors and/or to detect confounders. For example, if EEG and/or ECG data may be used to detect confounders. Visual images and/or video as may be obtained from a camera sensor may be used to aid in detecting sleep deprivation.

In another embodiment, the CI techniques described herein are implemented as a feature within a wearable device and/or smartphone. In one aspect, data may first be validated by a medical professional to validate or ensure accuracy of any CI estimation performed by the device. The medical professional may be a doctor or other individual with expertise in diagnosing and/or recognizing CI, cardiac conditions, etc. For example, the data and/or CI estimation may be validated by a doctor at a hospital or other medical facility where the doctor/medical professional uses clinical acumen and/or any associated testing. The validation may be performed using, or along, a scale of "quality of estimation." In one example, the scale for quality of estimation may range from A+ to D−, where A+ indicates a most believable and robust estimation. Once an estimate is obtained for a user, going forward, the significance of any feedback about health including any alarm generated by the device may be interpreted accordingly.

In another embodiment, the "quality of estimation" may be generalized to additional patients, e.g., all patients, having a profile similar to the profile of the user. For example, the relevant guidelines may be programmed on the device prior to sale or availability of the device. Once a device for a patient has collected sufficient data for the patient, based upon the user's bio-markers and historic profile, the device is capable of performing the CI (or fitness) interpretation accordingly.

The terminology used herein is for the purpose of describing particular embodiments only and is not intended to be limiting. Notwithstanding, several definitions that apply throughout this document now will be presented.

As defined herein, the singular forms "a," "an," and "the" are intended to include the plural forms as well, unless the context clearly indicates otherwise.

As defined herein, the term "another" means at least a second or more.

As defined herein, the terms "at least one," "one or more," and "and/or," are open-ended expressions that are both conjunctive and disjunctive in operation unless explicitly stated otherwise. For example, each of the expressions "at least one of A, B, and C," "at least one of A, B, or C," "one or more of A, B, and C," "one or more of A, B, or C," and "A, B, and/or C" means A alone, B alone, C alone, A and B together, A and C together, B and C together, or A, B and C together.

As defined herein, the term "automatically" means without user intervention.

As defined herein, the term "computer readable storage medium" means a storage medium that contains or stores program code for use by or in connection with an instruction execution system, apparatus, or device. As defined herein, a "computer readable storage medium" is not a transitory, propagating signal per se. A computer readable storage medium may be, but is not limited to, an electronic storage device, a magnetic storage device, an optical storage device, an electromagnetic storage device, a semiconductor storage device, or any suitable combination of the foregoing. Memory and/or memory elements, as described herein, are examples of a computer readable storage medium. A non-exhaustive list of more specific examples of a computer readable storage medium may include: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, or the like.

As defined herein, the term "coupled" means connected, whether directly without any intervening elements or indirectly with one or more intervening elements, unless otherwise indicated. Two elements may be coupled mechanically, electrically, or communicatively linked through a communication channel, pathway, network, or system.

As defined herein, the terms "includes," "including," "comprises," and/or "comprising," specify the presence of stated features, integers, steps, operations, elements, and/or components, but do not preclude the presence or addition of one or more other features, integers, steps, operations, elements, components, and/or groups thereof.

As defined herein, the term "if" means "when" or "upon" or "in response to" or "responsive to," depending upon the context. Thus, the phrase "if it is determined" or "if [a stated condition or event] is detected" may be construed to mean "upon determining" or "in response to determining" or "upon detecting [the stated condition or event]" or "in response to detecting [the stated condition or event]" or "responsive to detecting [the stated condition or event]" depending on the context.

As defined herein, the terms "one embodiment," "an embodiment," or similar language mean that a particular feature, structure, or characteristic described in connection with the embodiment is included in at least one embodiment described within this disclosure. Thus, appearances of the phrases "in one embodiment," "in an embodiment," and similar language throughout this disclosure may, but do not necessarily, all refer to the same embodiment. The terms "embodiment" and "arrangement" are used interchangeably within this disclosure.

As defined herein, the term "output" means storing in physical memory elements, e.g., devices, writing to display or other peripheral output device, sending or transmitting to another system, exporting, or the like.

As defined herein, the term "plurality" means two or more than two.

As defined herein, the term "processor" means at least one hardware circuit configured to carry out instructions contained in program code. The hardware circuit may be an integrated circuit. Examples of a processor include, but are not limited to, a central processing unit (CPU), an array processor, a vector processor, a digital signal processor (DSP), a field-programmable gate array (FPGA), a programmable logic array (PLA), an application specific integrated circuit (ASIC), programmable logic circuitry, and a controller.

As defined herein, the term "real time" means a level of processing responsiveness that a user or system senses as sufficiently immediate for a particular process or determination to be made, or that enables the processor to keep up with some external process.

As defined herein, the term "responsive to" means responding or reacting readily to an action or event. Thus, if a second action is performed "responsive to" a first action, there is a causal relationship between an occurrence of the first action and an occurrence of the second action. The term "responsive to" indicates the causal relationship.

As defined herein, the term "user" means a human being. The term user and "patient" are used interchangeably within this disclosure from time to time.

The terms first, second, etc. may be used herein to describe various elements. These elements should not be limited by these terms, as these terms are only used to distinguish one element from another unless stated otherwise or the context clearly indicates otherwise.

A computer program product may include a computer readable storage medium (or media) having computer readable program instructions thereon for causing a processor to carry out aspects of the present invention. Within this disclosure, the term "program code" is used interchangeably with the term "computer readable program instructions." Computer readable program instructions described herein may be downloaded to respective computing/processing devices from a computer readable storage medium or to an external computer or external storage device via a network, for example, the Internet, a LAN, a WAN and/or a wireless network. The network may include copper transmission cables, optical transmission fibers, wireless transmission, routers, firewalls, switches, gateway computers and/or edge devices including edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations for the inventive arrangements described herein may be assembler instructions, instruction-set-architecture (ISA) instructions, machine instructions, machine dependent instructions, microcode, firmware instructions, or either source code or object code written in any combination of one or more programming languages, including an object oriented programming language and/or procedural programming languages. Computer readable program instructions may specify state-setting data. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a LAN or a WAN, or the connection may be made to an external computer (for example, through the Internet using an Internet Service Provider). In some cases, electronic circuitry including, for example, programmable logic circuitry, an FPGA, or a PLA may execute the computer readable program instructions by utilizing state information of the computer readable program instructions to personalize the electronic circuitry, in order to perform aspects of the inventive arrangements described herein.

Certain aspects of the inventive arrangements are described herein with reference to flowchart illustrations and/or block diagrams of methods, apparatus (systems), and computer program products. It will be understood that each block of the flowchart illustrations and/or block diagrams, and combinations of blocks in the flowchart illustrations and/or block diagrams, may be implemented by computer readable program instructions, e.g., program code.

These computer readable program instructions may be provided to a processor of a computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. In this way, operatively coupling the processor to program code instructions transforms the machine of the processor into a special-purpose machine for carrying out the instructions of the program code. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the operations specified in the flowchart and/or block diagram block or blocks.

The computer readable program instructions may also be loaded onto a computer, other programmable data processing apparatus, or other device to cause a series of operations to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various aspects of the inventive arrangements. In this regard, each block in the flowchart or block diagrams may represent a module, segment, or portion of instructions, which comprises one or more executable instructions for implementing the specified operations. In some alternative implementations, the operations noted in the blocks may occur out of the order noted in the figures. For example, two blocks shown in succession may be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, may be implemented by special purpose hardware-based systems that perform the specified functions or acts or carry out combinations of special purpose hardware and computer instructions.

The corresponding structures, materials, acts, and equivalents of all means or step plus function elements that may be found in the claims below are intended to include any structure, material, or act for performing the function in combination with other claimed elements as specifically claimed.

The description of the embodiments provided herein is for purposes of illustration and is not intended to be exhaustive or limited to the form and examples disclosed. The terminology used herein was chosen to explain the principles of the inventive arrangements, the practical application or technical improvement over technologies found in the marketplace, and/or to enable others of ordinary skill in the art to understand the embodiments disclosed herein. Modifications and variations may be apparent to those of ordinary skill in the art without departing from the scope and spirit of the described inventive arrangements. Accordingly, reference should be made to the following claims, rather than to the foregoing disclosure, as indicating the scope of such features and implementations.

What is claimed is:

1. A method of detecting chronotropic incompetence, comprising:
   in response to receiving a user input specifying an estimate of activity level for the user, determining, using a processor, a baseline cardiac health measure for the user from a memory, wherein the baseline cardiac health measure includes a baseline validation factor for the user and corresponds to the estimate of activity level for the user;
   determining, using the processor, a validation factor for the user from first sensor data generated by a first sensor, wherein the first sensor data corresponds to a same time period as the estimate of activity level for the user;
   validating the estimate of activity level for the user with the validation factor by comparing the validation factor with the baseline validation factor;
   determining a cardiac health measure for the user from second sensor data generated by a second sensor corresponding to the same time period, wherein the first and second sensors are coupled to the processor;
   comparing the cardiac health measure for the user with the baseline cardiac health measure; and
   providing, using the processor, a signal indicating chronotropic incompetence for the user based upon the comparing of the cardiac health measure for the user with the baseline cardiac health measure.

2. The method of claim 1, further comprising:
   determining that the estimate of activity level for the user is in a defined range of activity level prior to determining the baseline cardiac health measure.

3. The method of claim 1, wherein the second sensor is a heart rate sensor and the cardiac health measure includes heart rate or a covariance calculated using heart rate.

4. The method of claim 1, wherein the estimate of activity level is a rate of perceived exertion for the user.

5. The method of claim 1, further comprising:
   automatically determining a confounder from sensor data comprising at least the second sensor data; and
   adjusting the comparing for the confounder.

6. The method of claim 5, wherein the confounder is sleep deprivation.

7. The method of claim 5, wherein the confounder is high stress.

8. The method of claim 1, wherein the first sensor is an accelerometer and the validation factor is expended energy of the user.

9. The method of claim 1, wherein the first sensor is a microphone and the validation factor is respiratory sound of the user.

10. An apparatus for detecting chronotropic incompetence, comprising:
    a first sensor configured to generate first sensor data;
    a second sensor configured to generate second sensor data;
    a memory configured to store the first and second sensor data and a baseline cardiac health measure; and
    a processor, coupled to the memory and the first sensor and the second sensor, wherein the processor is configured to:
    in response to receiving a user input specifying an estimate of activity level for the user, determine the baseline cardiac health measure for the user from the memory, wherein the baseline cardiac health measure includes a baseline validation factor for the user and corresponds to the estimate of activity level for the user;
    determine a validation factor for the user from first sensor data generated by a first sensor, wherein the first sensor data corresponds to a same time period as the estimate of activity level for the user;
    validate the estimate of activity level for the user with the validation factor by comparing the validation factor with the baseline validation factor;
    determine a cardiac health measure for the user from second sensor data generated by a second sensor corresponding to the same time period;
    compare the cardiac health measure for the user with the baseline cardiac health measure; and provide a signal indicating chronotropic incompetence for the user based upon the comparison of the cardiac health measure for the user with the baseline cardiac health measure.

11. The apparatus of claim 10, wherein the processor is further configured to:
determine that the estimate of activity level for the user is in a defined range of activity level prior to determining the baseline cardiac health measure.

12. The apparatus of claim 10, wherein the second sensor is a heart rate sensor and the cardiac health measure includes heart rate or a covariance calculated using heart rate.

13. The apparatus of claim 10, wherein the processor is further configured to:
automatically determine a confounder from sensor data comprising at least the second sensor data; and
adjust the comparing for the confounder.

14. The apparatus of claim 13, wherein the confounder is sleep deprivation.

15. The apparatus of claim 13, wherein the confounder is high stress.

16. The apparatus of claim 10, wherein the first sensor is an accelerometer and the validation factor is expended energy of the user.

17. The apparatus of claim 10, wherein the first sensor is a microphone and the validation factor is respiratory sound of the user.

18. A computer program product comprising a computer readable storage medium having program code stored thereon, the program code executable by a processor to perform operations for detecting chronotropic incompetence comprising:
in response to receiving a user input specifying an estimate of activity level for the user, determining a baseline cardiac health measure for the user from a memory, wherein the baseline cardiac health measure includes a baseline validation factor and corresponds to the estimate of activity level for the user;
determining a validation factor for the user from first sensor data generated by a first sensor, wherein the first sensor data corresponds to a same time period as the estimate of activity level for the user;
validating the estimate of activity level for the user with the validation factor by comparing the validation factor with the baseline validation factor;
determining a cardiac health measure for the user from second sensor data generated by a second sensor corresponding to the same time period, wherein the first and second sensors are coupled to the processor;
comparing the cardiac health measure for the user with the baseline cardiac health measure; and
providing a signal indicating chronotropic incompetence for the user based upon the comparing of the cardiac health measure for the user with the baseline cardiac health measure.

19. The computer program product of claim 18, wherein the program code is executable by the processor to perform operations further comprising:
determining that the estimate of activity level for the user is in a defined range of activity level prior to determining the baseline cardiac health measure.

20. The computer program product of claim 18, wherein the program code is executable by the processor to perform operations further comprising:
automatically determining a confounder from sensor data comprising at least the second sensor data; and
adjusting the comparing for the confounder.

21. A method of detecting chronotropic incompetence, comprising:
determining, using a processor, an estimate of activity level for a user from first sensor data generated by a first sensor;
determining, using the processor, a baseline cardiac health measure for the user from a memory, wherein the baseline cardiac health measure includes a baseline validation factor for the user and corresponds to the estimate of activity level for the user;
determining, using the processor, a validation factor for the user from second sensor data generated by a second sensor, wherein the second sensor data corresponds to a same time period as the estimate of activity level for the user and the first sensor data;
validating the estimate of activity level for the user with the validation factor by comparing the validation factor with the baseline validation factor;
determining a cardiac health measure for the user from third sensor data generated by a third sensor corresponding to the same time period, wherein the first, second, and third sensors and the memory are coupled to the processor;
comparing, using the processor, the cardiac health measure for the user with the baseline cardiac health measure; and
providing, using the processor, a signal indicating chronotropic incompetence for the user based upon the comparing of the cardiac health measure for the user with the baseline cardiac health measure.

22. The method of claim 21, further comprising:
determining that the estimate of activity level for the user is in a defined range of activity level prior to determining the baseline cardiac health measure.

23. The method of claim 21, wherein:
the first sensor is a microphone, the first sensor data is audio data specifying respiratory sound of the user, and the estimate of activity level for the user is determined from the audio data; and
the second sensor is an accelerometer and the validation factor is expended energy of the user.

24. The method of claim 21, wherein the third sensor is a heart rate sensor and the cardiac health measure includes heart rate or a covariance calculated using heart rate.

25. The method of claim 21, further comprising:
automatically determining a confounder from sensor data comprising at least the third sensor data; and
adjusting the comparing for the confounder.

26. The method of claim 21, wherein the confounder is sleep deprivation.

27. The method of claim 21, wherein the confounder is high stress.

* * * * *